US008771257B2

(12) United States Patent
Hoffman (10) Patent No.: US 8,771,257 B2
(45) Date of Patent: Jul. 8, 2014

(54) DRUG DELIVERY SHEATH (75) Inventor: David Hoffman, West Borough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2171 days.

(21) Appl. No.: 10/964,890

(22) Filed: Oct. 15, 2004

(65) Prior Publication Data

US 2006/0084910 A1    Apr. 20, 2006

(51) Int. Cl.
*A61M 39/00* (2006.01)

(52) U.S. Cl.
USPC .......................................... 604/537

(58) Field of Classification Search
USPC .............. 604/93.01–95.02, 232–234, 131, 604/192–198, 110, 537; 417/477.2; 128/203.15
See application file for complete search history.

(56) References Cited

U.S. PATENT DOCUMENTS

| | | | | | |
|---|---|---|---|---|---|
| 2,151,418 | A | * | 3/1939 | Bolte | 604/201 |
| 3,635,223 | A | * | 1/1972 | Klieman | 606/194 |
| 3,760,808 | A | * | 9/1973 | Bleuer | 604/14 |
| 4,331,146 | A | * | 5/1982 | Brignola | 604/200 |
| 4,632,673 | A | * | 12/1986 | Tiitola et al. | 604/415 |
| 4,700,692 | A | | 10/1987 | Baumgartner et al. | |
| 4,828,542 | A | * | 5/1989 | Hermann | 604/3 |
| 5,112,305 | A | * | 5/1992 | Barath et al. | 604/103.01 |
| 5,167,625 | A | * | 12/1992 | Jacobsen et al. | 604/891.1 |
| 5,242,397 | A | * | 9/1993 | Barath et al. | 604/103.01 |
| 5,279,565 | A | * | 1/1994 | Klein et al. | 604/105 |
| 5,336,178 | A | * | 8/1994 | Kaplan et al. | 604/509 |
| 5,364,356 | A | * | 11/1994 | Hofling | 604/103.01 |
| 5,533,505 | A | * | 7/1996 | Kallstrand et al. | 128/203.15 |
| 5,681,281 | A | * | 10/1997 | Vigil et al. | 604/103.01 |
| 5,713,863 | A | * | 2/1998 | Vigil et al. | 604/104 |
| 5,746,716 | A | * | 5/1998 | Vigil et al. | 604/97.01 |
| 5,823,183 | A | * | 10/1998 | Casper et al. | 128/203.15 |
| 5,873,852 | A | * | 2/1999 | Vigil et al. | 604/509 |
| 5,881,719 | A | * | 3/1999 | Gottenauer et al. | 128/203.15 |
| 5,893,840 | A | * | 4/1999 | Hull et al. | 604/103.02 |
| 5,988,163 | A | * | 11/1999 | Casper et al. | 128/203.15 |
| 6,048,332 | A | * | 4/2000 | Duffy et al. | 604/103.08 |
| 6,210,392 | B1 | * | 4/2001 | Vigil et al. | 604/507 |
| 6,401,712 | B1 | * | 6/2002 | von Schuckmann | 128/203.15 |
| 6,520,179 | B1 | * | 2/2003 | Von Schuckmann et al. | 128/203.15 |
| 6,544,221 | B1 | * | 4/2003 | Kokish et al. | 604/103.01 |

(Continued)

FOREIGN PATENT DOCUMENTS

JP    11319103    11/1999
WO    WO 01/23031 A    4/2001

*Primary Examiner* — Melanie Tyson
*Assistant Examiner* — Katelyn Bernier
(74) *Attorney, Agent, or Firm* — Fish & Richardson P.C.

(57) ABSTRACT

A cannulated drug delivery sheath having an annular wall and having a channel located within and extending partially through the annular wall. The annular wall defines a first lateral recess and a second lateral recess that are configured to respectively seat first and second cassettes containing therapeutic agents. The first and second lateral recesses have at least one first inlet port and at least one second inlet port, respectively. Also within the annular wall of the sheath is a first and second manifold. The first manifold is in fluid communication with the channel at one end and in fluid communication with the at least one first inlet port at another end. Similarly, the second manifold is in fluid communication with the channel at one end and in fluid communication with the at least one second inlet port at another end.

16 Claims, 7 Drawing Sheets

(56) References Cited

U.S. PATENT DOCUMENTS

| | | | |
|---|---|---|---|
| 6,656,155 B2 * | 12/2003 | Freyman | 604/103.01 |
| 6,695,830 B2 * | 2/2004 | Vigil et al. | 604/509 |
| 6,808,518 B2 * | 10/2004 | Wellman et al. | 604/507 |
| 7,048,714 B2 * | 5/2006 | Richter | 604/103.02 |
| 2002/0004641 A1 | 1/2002 | Bellhouse | |
| 2002/0082552 A1 | 6/2002 | Ding et al. | |
| 2004/0225247 A1 * | 11/2004 | Pugsley et al. | 602/41 |

* cited by examiner

DRUG DELIVERY SHEATH

FIELD OF THE INVENTION

The present invention relates to a device for aerosol delivery of therapeutic agents.

BACKGROUND OF THE INVENTION

Figure 1:
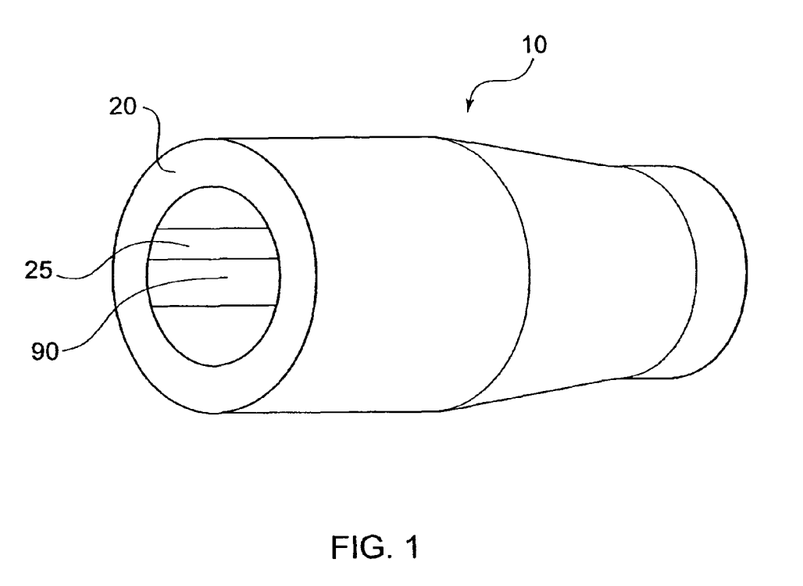
Figure 2:
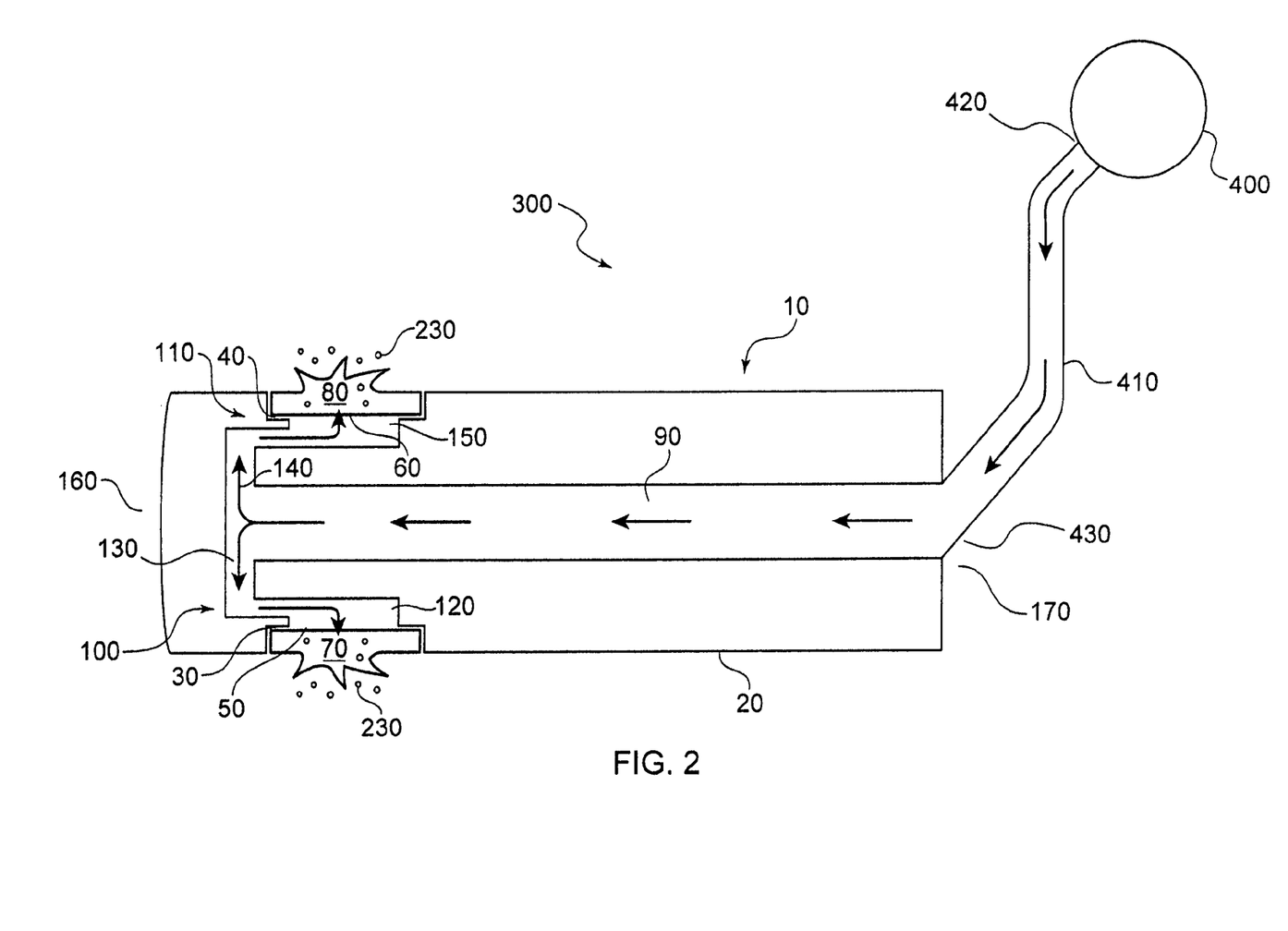

Therapeutic agents are often delivered directly to target sites of diseased tissue in various contemporary medical procedures. This direct delivery has proven to be an advantageous approach when treating numerous medical conditions. Advantages of this procedure are that only the target site may be exposed to the therapeutic and a controlled dose of therapeutic may be directly delivered to the target tissue.

Figure 3:
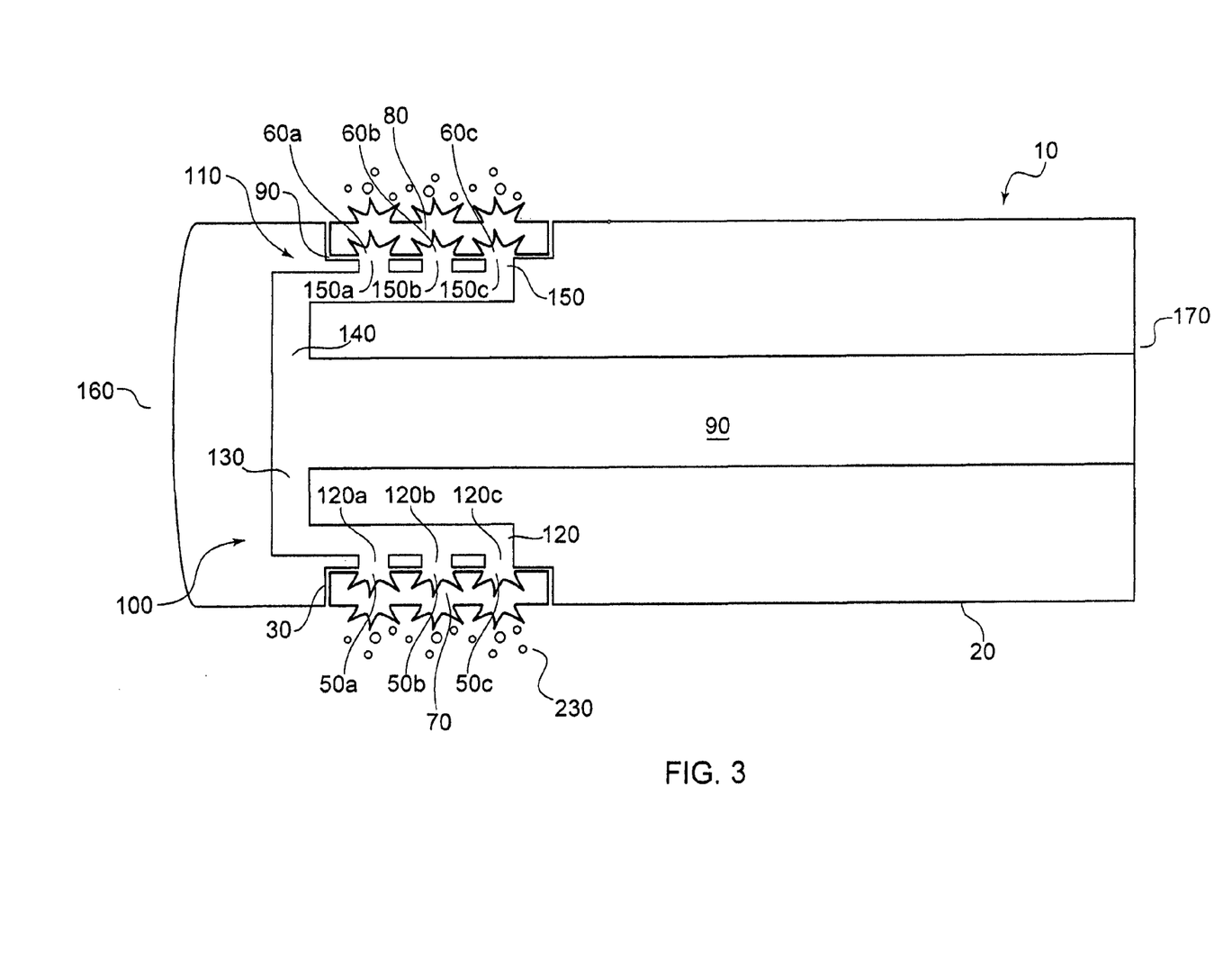
Figure 4:
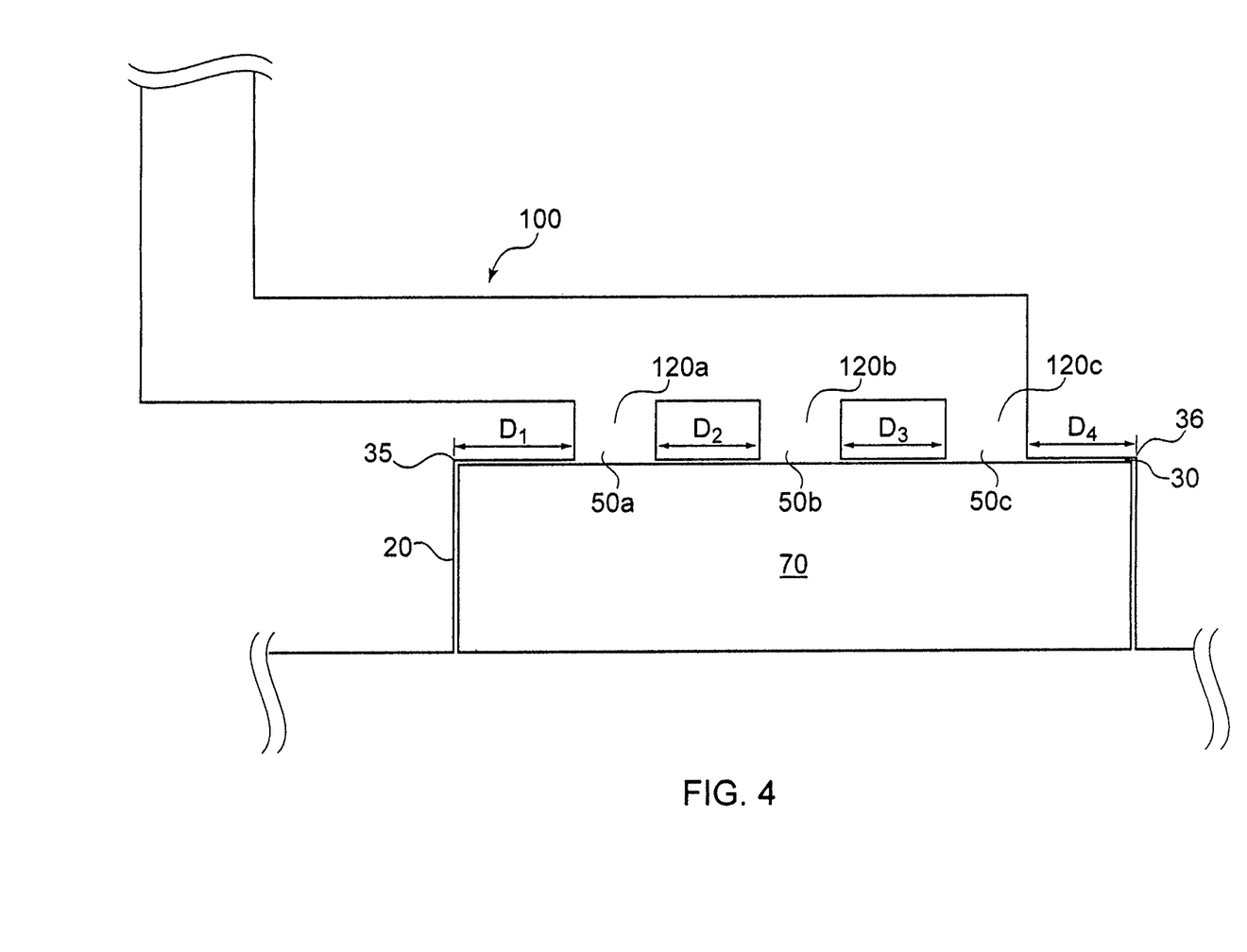
Figure 5:
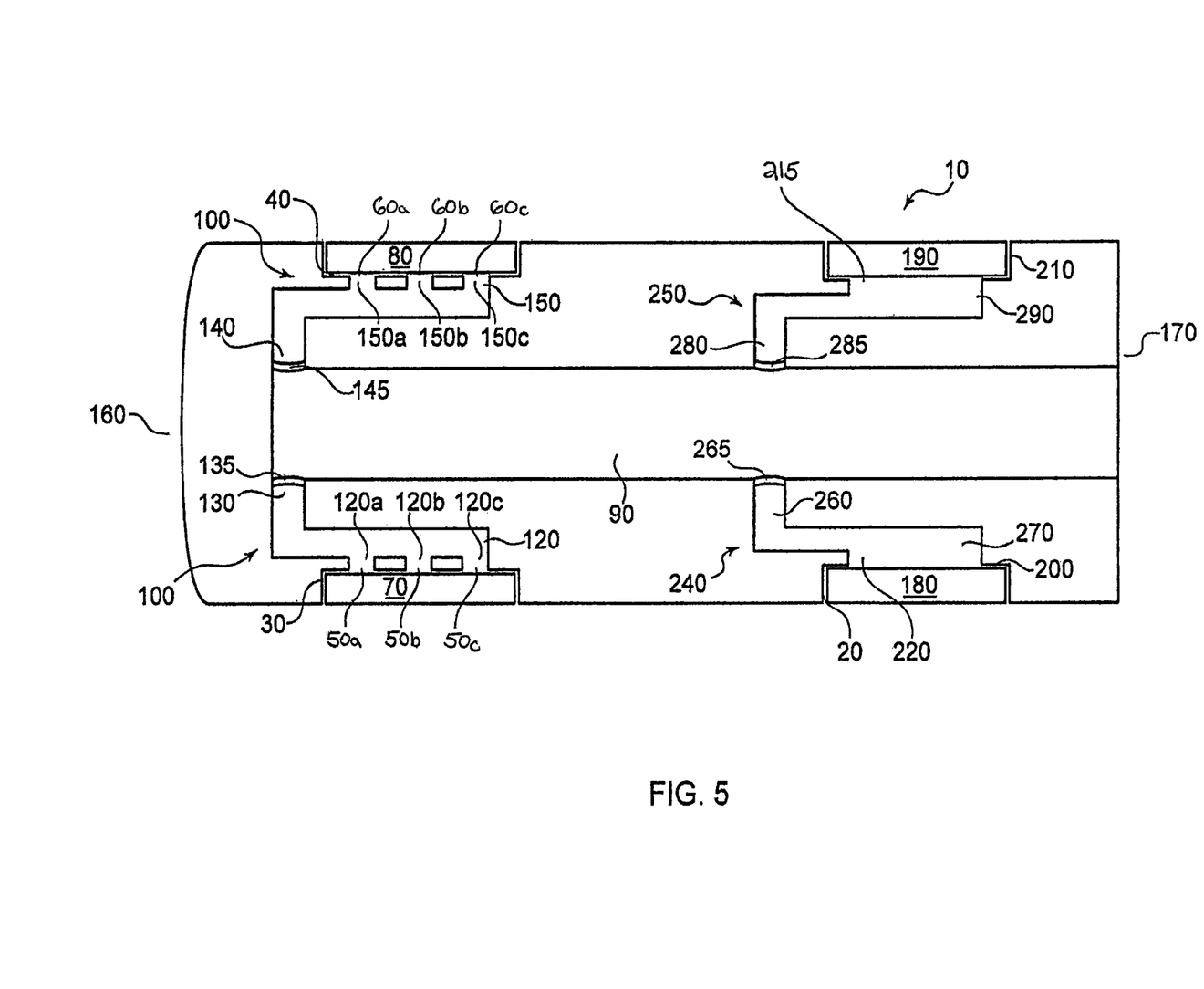
Figure 6:
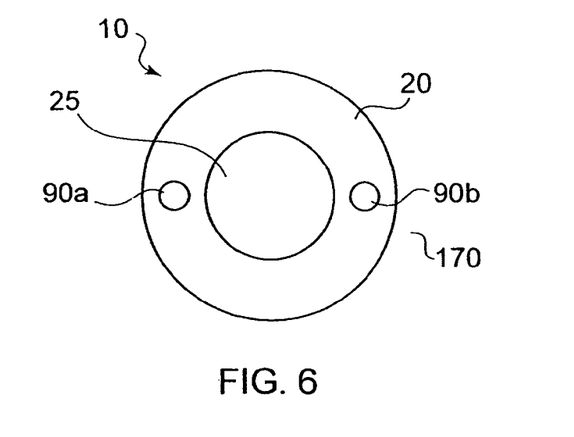
Figure 7:
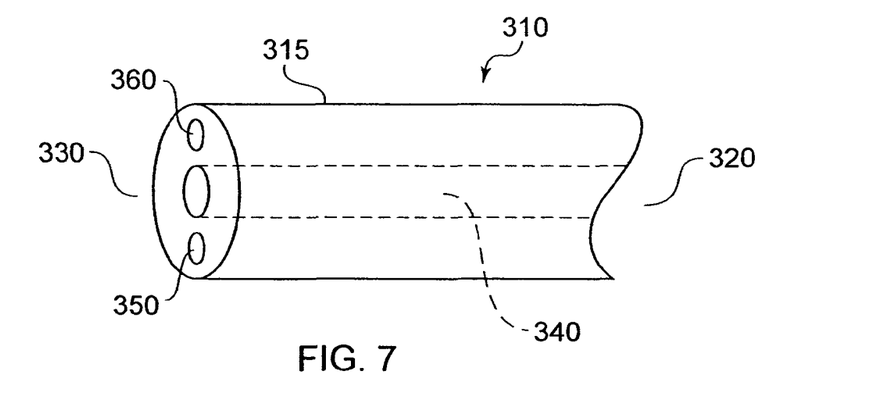
Figure 8:
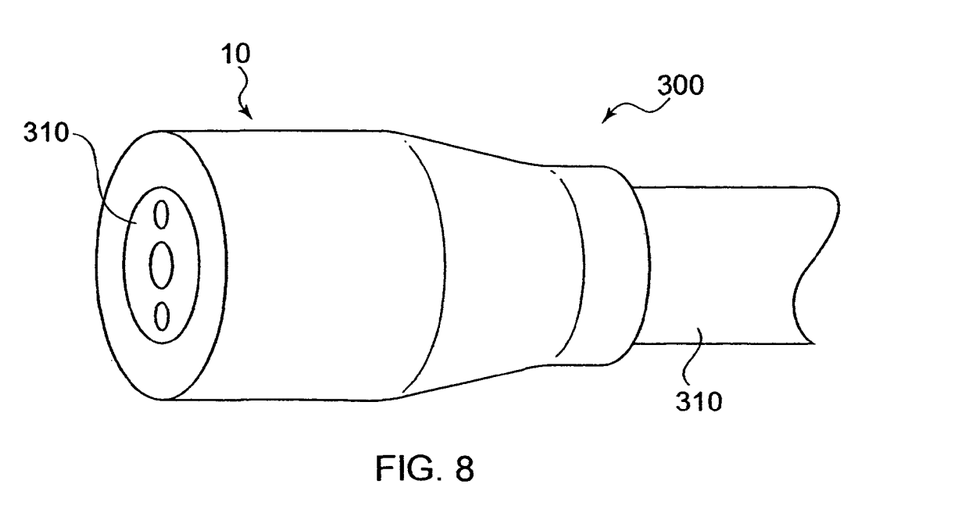
Figure 9:
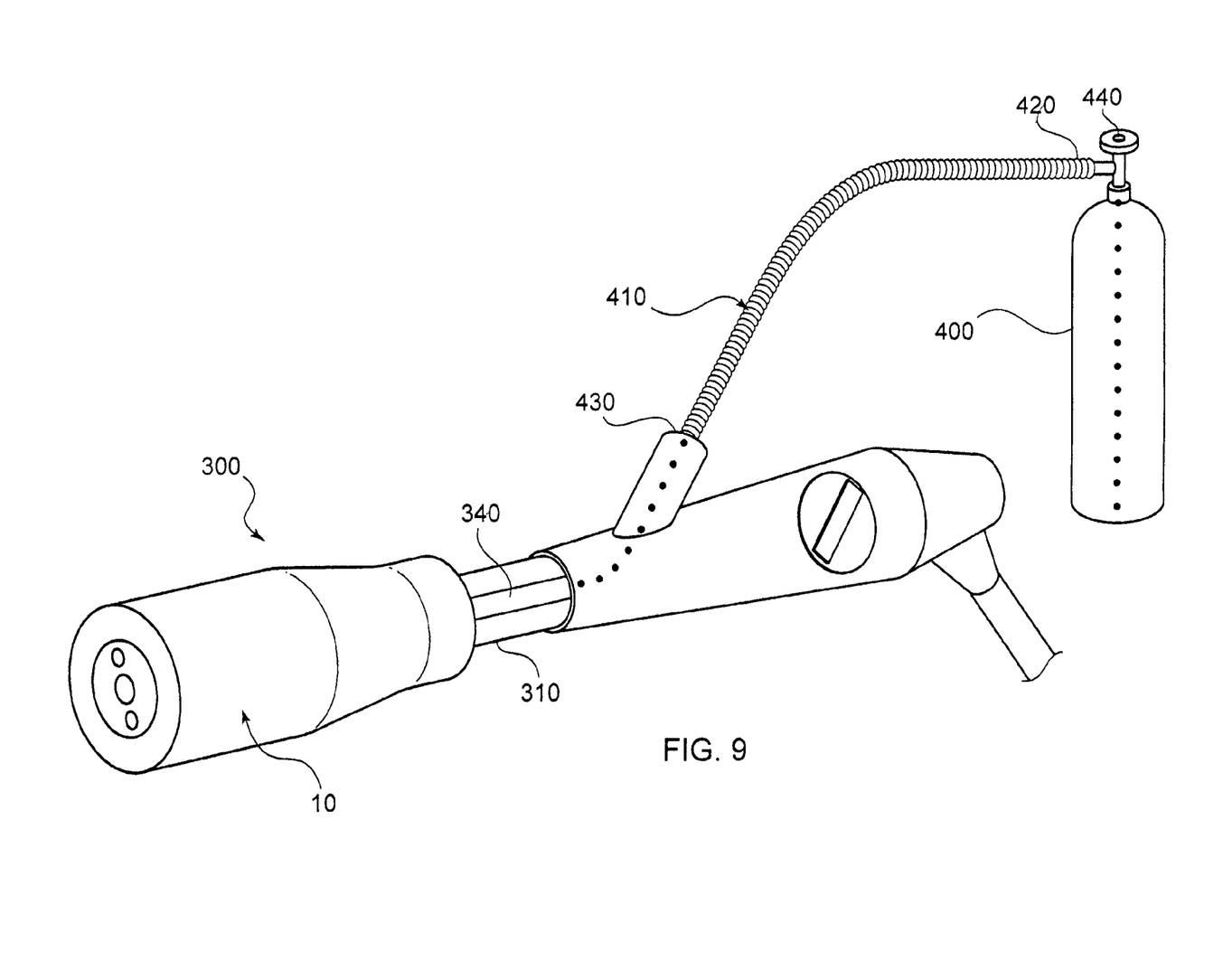

In the case of conventional anti-cancer therapeutics, many such therapeutics are inherently toxic, exposing both the patient and the healthcare provider to risks. Drug delivery systems can be used to improve the solubility and stability of drug solutions to eliminate mixing and to minimize exposure risks. Currently, drug delivery systems have been limited to inhalers and transdermal applications. The disadvantage of such systems are that they are limited to the specific drug used. Medical practice requires greater flexibility to use multiple drugs and dosing during the treatment regiment. Accordingly, there is a need for a delivery system to allow for such flexibility.

SUMMARY OF THE INVENTION

In an embodiment, the present invention provides a drug delivery sheath having an annular wall defining a cannula. The sheath comprises a channel located within and extending partially through the annular wall and first and second lateral recesses defined by the annular wall and configured to respectively seat first and second cassettes containing therapeutic agents. The first and second lateral recesses also each have at least one first and second inlet port, respectively. The sheath further comprises a first manifold and a second manifold. The first manifold is in fluid communication with the channel and in fluid communication with the at least one first inlet port, and the second manifold is in fluid communication with the channel and in fluid communication with the at least one second inlet port.

In an embodiment, the present invention provides a drug delivery sheath having an annular wall defining a cannula. The sheath comprises a first channel and a second channel located within and extending partially through the annular wall. The sheath further comprises first and second lateral recesses defined by the annular wall and configured to respectively seat first and second cassettes containing therapeutic agents. The first and second lateral recesses also each have at least one first and second inlet port, respectively. The sheath further comprises a first and second manifold. The first manifold is in fluid communication with the first channel and in fluid communication with the at least one first inlet port, and the second manifold is in fluid communication with the second channel and in fluid communication with the at least one second inlet port.

The present invention further provides drug delivery systems including a drug delivery sheath according to the present invention and an endoscope disposed within the cannula of the drug delivery sheath. The drug delivery systems may further comprise a pressurized gas source in fluid communication with the channel or channels of the drug delivery sheath.

The present invention also provides kits including a drug delivery sheath of the present invention and first and second cassettes that are configured to be inserted and seated into the first and second lateral recesses of the drug delivery sheath. Such cassettes may optionally be pre-filled with therapeutic agents.

BRIEF DESCRIPTION OF THE DRAWINGS

The present invention will become more fully understood from the detailed description given hereinbelow and the accompanying drawings which are given by way of illustration only and wherein:

FIG. 1 is a perspective view of an embodiment of a drug delivery sheath of the present invention.

FIG. 2 is a cross-sectional view of an embodiment of a drug delivery system of the present invention.

FIG. 3 is a cross-sectional view of a drug delivery sheath of the present invention illustrating an alternative embodiment of manifolds of the drug delivery sheath.

FIG. 4 is a cross-sectional view of an embodiment of a drug delivery sheath of the present invention depicting the distance between adjacent sub-channels of manifolds of the drug delivery sheath.

FIG. 5 is a cross-sectional view of an alternative embodiment of a drug delivery sheath of the present invention.

FIG. 6 is an end view of the distal end of an alternative embodiment of a drug delivery sheath of the present invention.

FIG. 7 is a perspective view of an endoscope of an embodiment of a drug delivery system of the present invention.

FIG. 8 is a perspective view of an embodiment of a drug delivery system of the present invention.

FIG. 9 is a perspective view of an embodiment of a drug delivery system of the present invention.

DETAILED DESCRIPTION OF THE INVENTION

Referring to FIG. 1, in one embodiment, the present invention provides a sheath 10 having a proximal end 160, a distal end 170, and an annular wall 20 defining a cannula 25 and comprising a channel 90 located within and extending partially through annular wall 20. Referring to FIG. 2, annular wall 20 defines a first lateral recess 30 having at least one first inlet port 50 and defines a second lateral recess 40 having at least one second inlet port 60. First and second lateral recesses 30 and 40 are configured to securely seat first and second rupturable cassettes 70 and 80, respectively, which each contain therapeutic agents 230 (some of the therapeutic agents 230 are shown released from cassettes 70 and 80 as explained in more detail below). Within annular wall 20 is a first manifold 100 and a second manifold 110 according to the present invention. First manifold 100 is in fluid communication with channel 90 at one end 130 and in fluid communication with at least one first inlet port 50 at another end 120. Similarly, second manifold 110 is in fluid communication with channel 90 at one end 140 and is in fluid communication with at least one second inlet port 60 at another end 150.

As indicated by the bold arrows in FIG. 2, sheath 10 is designed to receive pressurized gas that is introduced into channel 90 via a conduit 410 connected to a pressurized gas source 400 at one end 420 and in fluid communication with channel 90 at another end 430. The pressurized gas travels down channel 90 through first and second manifolds 100 and 110, through first and second inlet ports 50 and 60 to access and apply pressure to first and second cassettes 70 and 80. Such application of pressure causes first and second cassettes 70 and 80 to rupture, as schematically illustrated in FIG. 2, thereby releasing therapeutic agents 230 contained within first and second cassettes 70 and 80.

Manifolds 100 and 110, according to the present invention, may have any configuration so long as pressurized gas can access first and second cassettes 70 and 80. For example, referring to FIG. 3, in one embodiment, at least one first inlet port 50 comprises a plurality of first inlet ports 50*a*, 50*b*, and 50*c* and first manifold 100 comprises a plurality of first sub-channels 120*a*, 120*b*, and 120*c* that are each in fluid communication with a respective one of the plurality of first inlet ports 50*a*, 50*b*, and 50*c*. Alternatively or in addition, at least one second inlet port 60 comprises a plurality of second inlet ports 60*a*, 60*b*, and 60*c*, and second manifold 110 comprises a plurality of second sub-channels 150*a*, 150*b*, and 150*c* that are each in fluid communication with a respective one of the plurality of second inlet ports 60*a*, 60*b*, and 60*c*. Such a configuration allows the pressurized gas to be administered in a mist that can cover a larger surface area instead of a bolus that is limited to a specific location. This mist may or may not be controlled to allow a different stream of material to be applied. Each of the plurality of sub-channels of first manifold 100 and second manifold 110 may be separated from adjacent sub-channels 120*a-c* and 150*a-c*, respectively, by any distance. Referring to FIG. 4, to provide for a more even distribution of therapeutic agent 230 upon release from first cassettes 70, in a preferred embodiment, distances $D_1$, $D_2$, $D_3$, and $D_4$ are equal or substantially equal (where distance $D_1$ is the distance between sub-channel 120*a* and edge 35 of annular wall 20 defining first lateral recess 30; distance $D_2$ is the distance between sub-channel 120*a* and sub-channel 120*b*, distance $D_3$ is the distance between sub-channel 120*b* and sub-channel 120*c*, and distance $D_4$ is the distance between sub-channel 120*c* and edge 36 of annular wall 20 defining first lateral recess 30). The plurality of second sub-channels 150*a*, 150*b*, and 150*c*, may have similar configurations to provide for even distribution of therapeutic agent 230 from second cassette 80.

Sheath 10 may have any number of lateral recesses in any location in annular wall 20 in addition to first lateral recess 30 and second lateral recess 40 to seat additional cassettes carrying therapeutic agents. For example, referring to FIG. 5, in one embodiment, annular wall 20 of sheath 10 defines a third lateral recess 200 configured to securely seat a third rupturable cassette 180 containing therapeutic agents 230 and having at least one third inlet port 220. In addition, annular wall 20 of sheath 10 defines a fourth lateral recess 210 configured to securely seat a fourth rupturable cassette 190 containing therapeutic agents 230 and having at least one fourth inlet port 215. In this embodiment, a third manifold 240 is in fluid communication with channel 90 at one end 260 and is in fluid communication with at least one third inlet port 220 at another end 270. Similarly, a fourth manifold 250 is in fluid communication with channel 90 at one end 280 and is in fluid communication with at least one fourth inlet port 230 at another end 290. Similar to FIG. 3, at least one third inlet port 220 and/or at least one fourth inlet port 215 may comprise a plurality of inlet ports and third manifold 240 and/or fourth manifold 250 may comprise a plurality of sub-channels that are in fluid communication with respective ones of the plurality of inlet ports. Similar to FIG. 4, the distance between each of the plurality of sub-channels and therefore the distance between each of the plurality of inlet ports may be equal or substantially equal to provide for a more even distribution of therapeutic agents upon release from the respective cassette.

Sheath 10 may also have any number of channels 90 located within and extending partially through any side of annular wall 20 that are in communication with any number of manifolds. For example, referring to FIG. 6, which is an end view of distal end 170 of another embodiment of sheath 10, two channels 90*a* and 90*b* extend through annular wall 20 and each are in fluid communication with separate manifolds. Each separate manifold is, in turn, in fluid communication with a separate recess, which holds a cassette containing therapeutic agents. Such an embodiment provides for selective release of therapeutic agents from their respective cassettes, as pressurized gas can be exclusively introduced into either channel 90*a* or 90*b* which will ultimately direct the pressurized gas to the cassette containing the desired therapeutic agent to be released.

In another embodiment that also provides for selective release of therapeutic agents from their respective cassettes, manifolds of any of the embodiments of the present invention comprise valves which can be opened and closed to provide or prevent access of the pressurized gas through the manifolds. For example, referring back to FIG. 5, in one embodiment, first manifold 100 comprises a valve 135 at end 130, second manifold 110 comprises a valve 145 at end 140, third manifold 240 comprises valve 265 at end 260, and fourth manifold 250 comprises valve 285 at end 280. If it is desired to only release therapeutic agent 230 from first cassette 70, for example, then valves 145, 265, and 285 can be closed and valve 135 can be opened to allow the pressurized gas to travel down main channel 90 through first manifold 100 only and then through inlet ports 50*a*-50*c* to access and apply pressure to first cassette 70 only, thereby releasing therapeutic agents 230 from first cassette 70 only. Of course, it is understood that any of the other valves may be opened and the remaining other valves may be closed to provide selective release of therapeutic agents 230 from any of the other cassettes.

Because sheath 10 has an annular wall 20 defining a cannula 25 and because channel 90 is located within annular wall 20 so that cannula 25 is unobstructed, sheath 10 of the present invention allows any instrument to be disposed within cannula 25. For example, referring to FIGS. 7 and 8, in one embodiment, the present invention provides a drug delivery system 300 comprising an endoscope 310 disposed within cannula 25 of sheath 10. Endoscope 310 comprises a rigid or flexible shaft 315 having a proximal end 320, a distal end 330, and a working channel 340 extending therethrough. Endoscope 310 may also comprise any number of additional components, such as one or more light sources, visioning systems, and other tools, such as diagnostic and treatment devices that are inserted into working channel 340 (or one of a plurality of working channels 340). For example, referring to FIG. 7, in one embodiment, endoscope 310 has a light source 350 and a vision chip 360 at distal end 330. Light source 350 is used to illuminate an area of which an image is to be taken and vision chip 360 obtains image information and passes video image data via electrical leads contained within shaft 315 to appropriate circuitry that will digitize the video data and communicate that data to a computer having suitable software to format the data and cause it to be displayed on a video display system located external to endoscope 310.

The present invention also provides for drug delivery systems that include a pressurized gas source that is in fluid communication with channel 90 of sheath 10. For example, referring to FIG. 9, drug delivery system 300 (described above) may further comprise a pressurized gas source 400 and a conduit 10 connected to pressurized gas source 400 at one end 420 and in fluid communication with working channel 340 of endoscope 310 at another end 430. Working channel 340 is, in turn, in fluid communication with channel 90 of sheath 10. Referring to FIG. 2, in an alternative embodiment, drug delivery system 300 comprises a pressurized gas source 400 and a conduit 410 connected to pressurized gas source at one end 420 and directly connected to channel 90 of sheath 10 at another end 430. In either embodiment of drug delivery system 300, pressurized gas source 400 may include an actuator valve 440 (shown in FIG. 9) which can be opened to release pressurized gas from the pressurized gas source 400 and can be closed to prevent release of further pressurized gas once a desired amount of pressurized gas has been released. Drug delivery system 300 of the present invention may comprise additional conduits 410 in embodiments where sheath 10 comprises more than one channel 90 so that a separate conduit is associated with each channel 90. In such embodiments, actuator valve 440 or more than one actuator valve 440 can be used to regulate the passage of the pressurized gas through the appropriate conduit 410 to reach and pass through the desired channel 90. Because the pressurized gas ultimately enters into the cassettes containing therapeutic agents and therefore comes into contact with the therapeutic agents, the pressurized gas is sterilized air or any other liquid or gas that is biocompatible with the therapeutic agent.

The present invention also provides kits comprising sheath 10 and cassettes 70 and 80 for placement in lateral recesses 30 and 40, respectively, of annular wall 20. Such kits may include as many cassettes as there are recesses defined in annular wall 20. For example, in embodiments where annular wall 20 additionally defines third and fourth lateral recesses 200 and 210, kits of the present invention include cassettes 180 and 190 for respective placement in recesses 200 and 210. The cassettes may be pre-filled with therapeutic agents 230 or may be empty and include a sealable port through which therapeutic agents 230 may be introduced. All cassettes may contain the same or different therapeutic agents 230 and any cassette may contain a combination of different therapeutic agents.

The therapeutic agents 230 of the present invention contained within the cassettes of the present invention may be any pharmaceutically acceptable agents such as non-genetic therapeutic agents, biomolecules, small molecules, or cells. Any of the therapeutic agents may be combined to the extent such combination is biologically compatible.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosporine, cisplatin, vinblastine, vincristine, epothilones, endostatin, trapidil, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, dicumarol, aspirin, prostaglandin inhibitors, platelet inhibitors and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p2'7, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds having a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

With respect to delivery of genetically engineered cells, the present invention provides a less invasive method of delivering genetically engineered cells to a target site compared to the conventional delivery of engineered cells using matrices or scaffold sheets of engineered tissue. Furthermore, the present invention provides for direct contact of the engineered cells with the cells at the target site. The cassettes may contain the engineered cells in addition to other agents to aid in the healing process such as antibiotics, anesthetic agents, and growth enhancing agents.

The therapeutic agents of the present invention may be micronized or microencapsulated to provide for sustained release. Specifically, the therapeutic agents may be micronized by destructive or constructive methods, where non-limiting examples of destructive methods include crushing and grinding, granulation, and spray formation and non-limiting examples of constructive methods include evaporation/condensation, physico-chemical methods, crystallization, and vapor condensation. The therapeutic agents of the present invention may also be microencapsulated in a polymer shell. Such microencapsulation may be performed by phase separation processes such as simple coacervation in an aqueous medium, complex coacervation in an aqueous medium, coacervation in a non-aqueous medium; interface polycondensation processes such as pan coating, fluid bed coating, and air-suspension coating; and matrix solidification processes such as spray drying, spray congealing, solvent evaporation, and spray polycondensation. The therapeutic agents may also be adsorbed onto small carrier particles.

The polymer or polymers used in the present invention to encapsulate the therapeutic agent are preferably capable of absorbing a substantial amount of drug solution and may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Encapsulation from polymer dispersions such as polyurethane dispersions (BAYHYDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference.

The therapeutic agents contained within the cassettes can be delivered to any target site in the body, particularly any endoluminal target sites such as the gastrointestinal, vascular, or air exchange lumens. Other target sites include the, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

The therapeutic agents can be used, for example, in any application for treating, preventing, or otherwise affecting the course of a disease or tissue or organ dysfunction. For example, the sheath of the present invention can by used to induce or inhibit angiogenesis, as desired, to present or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

The foregoing description and example have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention are within the scope of the present invention.

I claim:

1. A drug delivery system comprising:
   a sheath comprising:
      an annular wall defining a cannula having at least one channel extending partially therethrough;
      at least one lateral recess comprising:
         a first lateral recess defined by the annular wall and seating a first rupturable cassette containing therapeutic agents, the first lateral recess having at least one first inlet port;
         a second lateral recess defined by the annular wall and seating a second rupturable cassette containing therapeutic agents, the second lateral recess having at least one second inlet port; and
      at least one manifold comprising:
         a first manifold in fluid communication with the at least one channel and in fluid communication with the at least one first inlet port; and
         a second manifold in fluid communication with the at least one channel and in fluid communication with the at least one second inlet port; and
   a pressurized gas source comprising:
      an actuator valve; and
      a conduit connecting the pressurized gas source to the at least one channel of the sheath;
   wherein, prior to an introduction of pressurized gas into the at least one channel, the first rupturable cassette contains therapeutic agents and the second rupturable cassette contains therapeutic agents.

2. The drug delivery system of claim 1, wherein the at least one first inlet port comprises a plurality of first inlet ports.

3. The drug delivery system of claim 2, wherein the first manifold comprises a plurality of first sub-channels, each of the plurality of first sub-channels in fluid communication with a respective one of the plurality of first inlet ports.

4. The drug delivery system of claim 1, wherein the at least one second inlet port comprises a plurality of second inlet ports.

5. The drug delivery system of claim 4, wherein the second manifold comprises a plurality of second sub-channels, each of the plurality of second sub-channels in fluid communication with a respective one of the plurality of second inlet ports.

6. The sheath of claim 1 wherein the at least one lateral recess further comprises:
   a third lateral recess defined by the annular wall and configured to seat a third rupturable cassette containing therapeutic agents, the third lateral recess having at least one third inlet port;
   a fourth lateral recess defined by the annular wall and configured to seat a fourth rupturable cassette containing therapeutic agents, the fourth lateral recess having at least one fourth inlet port; and
wherein the at least one manifold further comprises:
   a third manifold in fluid communication with the at least one channel and in fluid communication with the at least one third inlet port; and
   a fourth manifold in fluid communication with the at least one channel and in fluid communication with the at least one fourth inlet port; and
further comprising:
   a third rupturable cassette configured to be seated in the third lateral recess; and
   a fourth rupturable cassette configured to be seated in the fourth lateral recess.

7. The sheath of claim 6, wherein the third and fourth rupturable cassettes contain therapeutic agents.

8. The drug delivery system of claim 1, wherein the therapeutic agents contained within the first rupturable cassette and the second rupturable cassette are engineered cells.

9. The drug delivery system of claim 1, wherein therapeutic agents contained within each of the first rupturable cassette and the second rupturable cassette are a combination of engineered cells, antibiotics, and anesthetic agents.

10. The drug delivery system of claim 1, wherein the therapeutic agents contained within the first rupturable and second rupturable cassettes are microencapsulated.

11. A drug delivery system comprising:
    the sheath of claim 1; and
    an endoscope disposed within the cannula of the sheath of claim 1, the endoscope comprising a shaft having a proximal end, a distal end and a working channel extending therethrough.

12. The drug delivery system of claim 11, wherein the distal end of the endoscope comprises a light source.

13. The drug delivery system of claim 11, wherein the distal end of the endoscope comprises a vision chip.

14. The drug delivery system of claim 11, further comprising:
    a pressurized gas source comprising an actuator valve; and
    a conduit connected to the pressurized gas source at one end and in fluid communication with the working channel of the endoscope at another end, the working channel in fluid communication with the at least one channel of the sheath.

15. The drug delivery system of claim 14, wherein the pressurized gas is sterilized air.

16. The sheath of claim 1, wherein the at least one channel comprises a first channel and a second channel, and wherein the first manifold is in fluid communication with the first channel and the second manifold is in fluid communication with the second channel.

* * * * *

UNITED STATES PATENT AND TRADEMARK OFFICE
CERTIFICATE OF CORRECTION

| | | Page 1 of 1 |
|---|---|---|
| PATENT NO. | : 8,771,257 B2 | |
| APPLICATION NO. | : 10/964890 | |
| DATED | : July 8, 2014 | |
| INVENTOR(S) | : David Hoffman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2301 days.

Signed and Sealed this
Sixth Day of October, 2015

Michelle K. Lee
*Director of the United States Patent and Trademark Office*